US008824625B2

(12) United States Patent
Ullberg

(10) Patent No.: US 8,824,625 B2
(45) Date of Patent: Sep. 2, 2014

(54) COMPUTED TOMOGRAPHY SCANNING SYSTEM

(75) Inventor: Christer Ullberg, Sollentuna (SE)

(73) Assignee: Xcounter AB, Danderyd (SE)

( * ) Notice: Subject to any disclaimer, the term of this patent is extended or adjusted under 35 U.S.C. 154(b) by 230 days.

(21) Appl. No.: 13/257,068

(22) PCT Filed: Apr. 29, 2010

(86) PCT No.: PCT/SE2010/050474
§ 371 (c)(1),
(2), (4) Date: Sep. 16, 2011

(87) PCT Pub. No.: WO2010/126445
PCT Pub. Date: Nov. 4, 2010

(65) Prior Publication Data
US 2012/0008738 A1   Jan. 12, 2012

Related U.S. Application Data

(60) Provisional application No. 61/213,026, filed on Apr. 29, 2009.

(30) Foreign Application Priority Data

Apr. 29, 2009 (SE) ...................................... 0950288

(51) Int. Cl.
*A61B 6/03* (2006.01)
*A61B 6/04* (2006.01)
(52) U.S. Cl.
USPC .............................................. 378/19; 378/37
(58) Field of Classification Search
USPC .................... 378/19, 37, 26, 22, 62
See application file for complete search history.

(56) References Cited

U.S. PATENT DOCUMENTS

| | | |
|---|---|---|
| 5,379,336 A | 1/1995 | Kramer et al. |
| 6,292,531 B1 | 9/2001 | Hsieh |
| 6,483,890 B1 | 11/2002 | Malamud |
| 6,933,505 B2 | 8/2005 | Vuorela |
| 7,170,062 B2 | 1/2007 | Vuorela |
| 7,189,971 B2 | 3/2007 | Spartiotis et al. |
| 7,361,881 B2 | 4/2008 | Spartiotis |
| 2004/0000630 A1 | 1/2004 | Spartiotis et al. |
| 2004/0141588 A1 | 7/2004 | Francke et al. |
| 2006/0011853 A1 | 1/2006 | Spartiotis et al. |
| 2006/0071174 A1 | 4/2006 | Spartiotis et al. |
| 2006/0104415 A1 | 5/2006 | Unger et al. |
| 2007/0019784 A1 | 1/2007 | Ting |
| 2008/0019477 A1 | 1/2008 | Spartiotis et al. |
| 2009/0080604 A1 | 3/2009 | Shores et al. |

OTHER PUBLICATIONS

International Search Report, PCT/SE2010/050474, Oct. 6, 2010.

*Primary Examiner* — Irakli Kiknadze
(74) *Attorney, Agent, or Firm* — Myers Bigel Sibley & Sajovec, PA

(57) ABSTRACT

A system for recording CT data of an object in an object area (4) comprises an X-ray source (5) and an X-ray detector (6) at either side of the object area. The X-ray detector comprises a stack of elongated detector array arrangements (6a) arranged in parallel and provided for detecting X-rays (9a) from the X-ray source transmitted through the object, thus recording images of the object. A device (10a) is provided for rotating the X-ray source (5) and the X-ray detector (6) around an axis of rotation which is parallel with the elongated detector array arrangements, while the elongated detector array arrangements are provided for imaging the object repeatedly. Further, either the elongated detector array arrangements are moved within the X-ray detector or the axis of rotation is moved during the rotation to thereby provide for the elongated detector array arrangements to record the CT data.

21 Claims, 5 Drawing Sheets

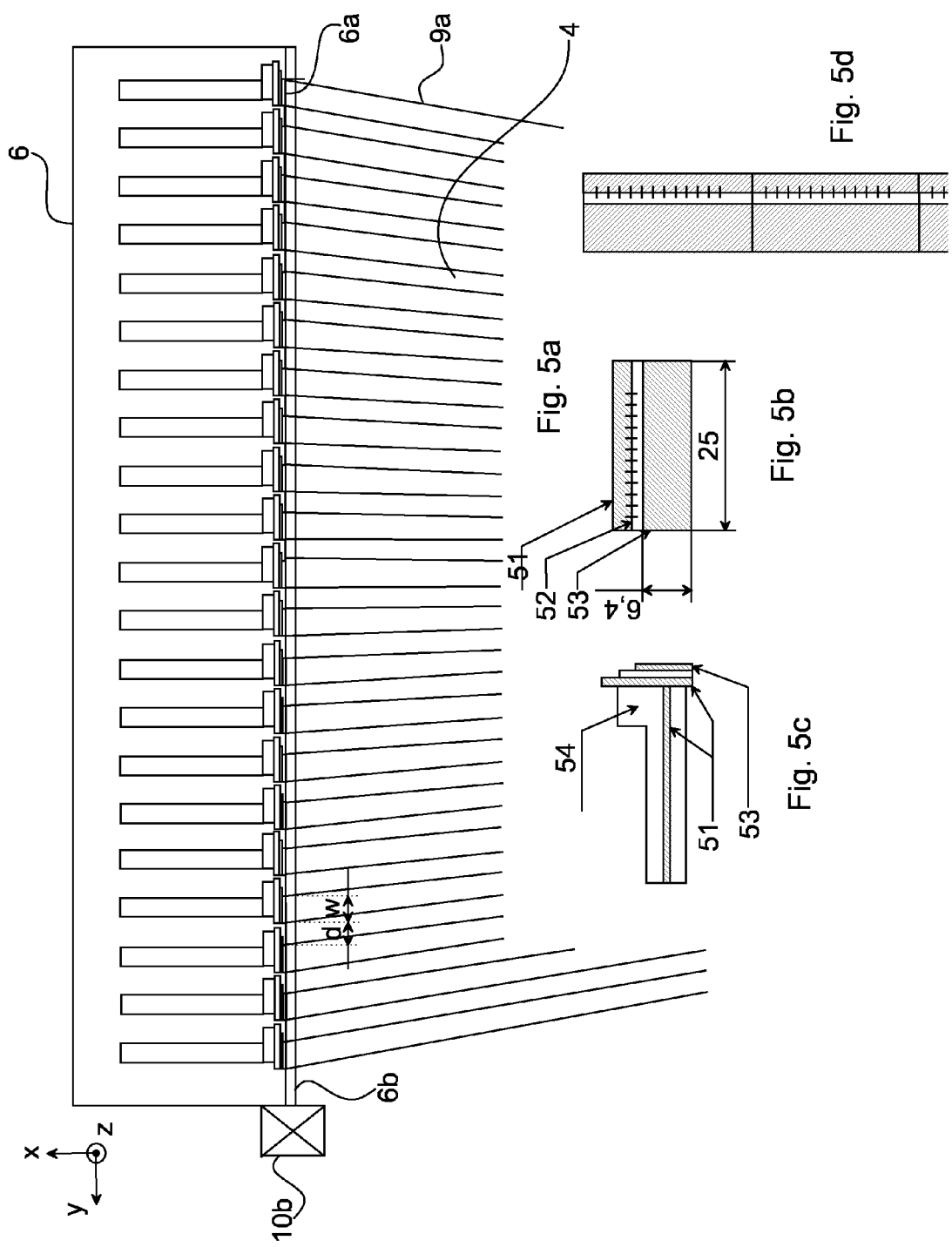

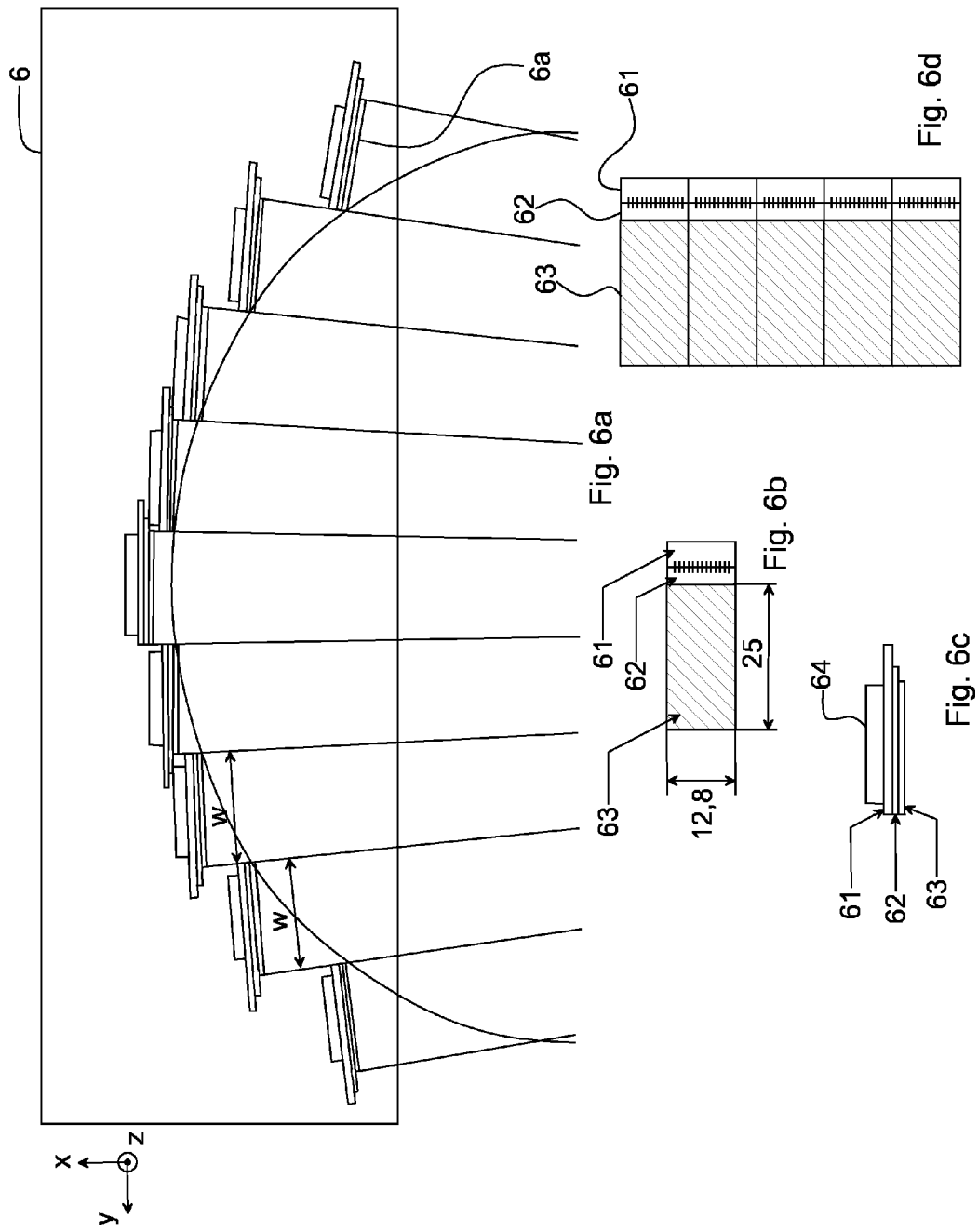

COMPUTED TOMOGRAPHY SCANNING SYSTEM

CROSS REFERENCE TO RELATED APPLICATIONS

This application is a 35 U.S.C. §371 national stage application of PCT International Application No. PCT/SE2010/050474, filed on 29 Apr. 2010, which itself claims priority to Swedish Application No. 0950288-1, filed 29 Apr. 2009 and U.S. provisional Patent Application No. 61/213,026, filed 29 Apr. 2009, the disclosure and content of all of which are incorporated by reference herein in their entirety.

FIELD OF THE INVENTION

The present invention relates to the field of computed tomography, and in particular to a computed tomography scanning system for recording computed tomography image data of an object.

BACKGROUND OF THE INVENTION

Computed tomography scanning (CT scanning), also denoted computerized tomography or computed axial tomography (CAT), is a medical imaging method employing imaging by sectioning or 3D reconstruction. In the CT-scanning an X-ray source and an X-ray detector are arranged opposite one another on an arrangement that rotates around a patient. The X-ray source transmits radiation through the patient and the X-ray detector measures the attenuated radiation. The radiation is converted to an electrical signal, a computer processes these signals and the desired images can be provided.

An important improvement of the two-dimensional scanning was made with the introduction of the so-called spiral or helical scan. Instead of scanning the patient on a two-dimensional basis, the patient is scanned on a three-dimensional basis. In particular, the table on which the patient rests moves through the scanning field at a constant speed while the X-ray tube and X-ray detector rotates around the patient. Digital geometry processing is used to generate a three-dimensional image of the internals of an object from a large series of two-dimensional X-ray images taken around a single axis of rotation.

The X-ray arrangement is rotated one revolution, then moved a small step and rotated again. Alternatively, in the spiral scan the X-ray arrangement moves in a helical movement with a small pitch for each revolution. The speed of rotation is normally a few revolutions per second.

SUMMARY OF THE INVENTION

CT systems of today use rather narrow detectors with a small field of view in the translation direction. The detector is typically only 0.5-30 mm wide. There is a desire in CT imaging to make the detector wider in order to reduce the number of revolutions needed to image the organ or object of interest. The existing CT detectors use light sensitive CMOS detectors with scintillators emitting light when struck by X-rays. This detector technology cannot be used for implementing wide detectors due to the high costs and problems to read out the signals from a wider detector. An alternative being investigated is the use of area detectors, so called cone beam CT. These area detectors are made of for example thin film transistor (TFT) panels. Such TFT-panels are currently used for 2D X-ray imaging.

However, the TFT-panels have a number of limitations when it comes to cone beam CT imaging. Firstly, they are slow to read out and can at most be read out 60 times per second, but then with rather large pixel size. Small pixel sizes can typically only be read out 5-10 times per second. This is far too slow for CT applications when one wishes to read out the detector one thousand times per revolution or more. Secondly, the TFT-panels have too high electronic noise, which adds up when thousands of images are combined to form the CT slice images or 3D volumes. Thirdly, area detectors are sensitive to X-rays that scatter in the patient and hit the detector in an arbitrary position, causing a foggy appearance in the X-ray images. These scattered X-rays are normally suppressed by arranging a grid between the patient and the detector. The grid is moved much faster than the detector readout frequency in order to prevent a shadow image to be formed from the grid. When it comes to area detectors that need to be read out thousands of times each second it is both difficult to construct a grid that shields well enough and that can be moved much faster than the readout frequency without causing artefacts in the images. Fourthly, the TFT detectors have residual ghost images present that add noise to the succeeding images. They also often saturate for high X-ray fluxes causing the signal to bloom out over several pixels.

It would be desirable to provide cone beam CT-scanning in which a larger number of images could be taken without degrading the image quality, more specifically somewhere between 100 and 5000 images in each rotation of the X-ray arrangement, when rotating 0.1-1 revolutions per second. This would set high demands on the detector, for example in terms of readout speed. The detector would have to be able to rapidly detect radiation transmitted from the X-ray source and to quickly transfer the data from the detector to a buffer memory or to a computer from each readout. Further, in order to obtain usable images, that is, images having a high enough resolution, the size of the pixels have to be small, preferably within the range of 0.05-0.1 mm. The detectors used in cone beam CT-scanning today cannot meet these demands; they are simply not fast enough to take such high-resolution images at the required speed.

Further yet, the detector used in a cone beam CT-scanning has to be able to shield radiation scattered from the object being imaged. As mentioned, scattered radiation appears as noise and is added in the reconstructed image. It is difficult to prevent this kind of noise; it is for example difficult to efficiently shield the detector by means of a grid or the like.

In medical applications of X-ray imaging it is important to minimize the radiation dose that the patient is subjected to. It is also important that the examination procedure is as comfortable as possible and that the procedure is carried out as fast as possible.

Further, it is important that the X-ray imaging system can be manufactured at a reasonable cost.

In view of the above it would be desirable to provide an in many aspects improved arrangement and system for imaging objects, and in particular medical imaging by means of cone beam computed tomography.

It is an object of the invention to provide a computed tomography scanning system for recording computed tomography image data that overcomes, or at least alleviates, the shortcomings of the prior art. In particular, an object is to provide a computed tomography scanning system wherein an increased quality of images recorded can be provided, while still enabling the imaging procedure to be performed quickly.

It is another object of the invention to provide such system, the construction of which is less complicated. In particular, it is an object to provide a system wherein the need for shielding devices can be relaxed.

It is yet another object to increase the quality in terms of resolution and noise levels of the images recorded, thereby increasing the quality of a conclusion drawn or a diagnosis made based on the images.

Still another object of the invention is to lessen the discomfort of the patient undergoing an examination in the form of imaging a body part, such as a breast.

These objects, among others, are achieved by systems as claimed in the appended patent claims.

In accordance with the invention there is provided a system for recording CT data of an object in an object area. The system comprises an X-ray source and an X-ray detector at either side of the object area. The X-ray detector comprises a stack of elongated detector array arrangements or line detectors arranged in parallel and provided for detecting X-rays from the X-ray source transmitted through the object, thus recording images of the object. A device is provided for rotating the X-ray source and the X-ray detector around an axis of rotation which is parallel with the elongated detector array arrangements, while the elongated detector array arrangements are provided for imaging the object repeatedly. Further, either the elongated detector array arrangements are moved within the X-ray detector during the rotation or the axis of rotation is moved during the rotation to thereby provide for the elongated detector array arrangements to record the CT data.

The imaging arrangement in accordance with the present invention can be read out 300-1000 times per second or even faster. The resolution is high and the pixel size is small, down to 0.05 mm. The photon counting solid state detector ensures that there is no noise contributing to the image, besides the statistical fluctuation of the X-ray photon flux. The detector can also be used in energy integrating mode since the noise from this detector is sufficiently low. The detector has no lag, ghosting or blooming effects. Further, the performance of the imaging arrangement is not degraded by scattered radiation. The line detectors discriminate more than 95% of the scattered photons. Further yet, the imaging arrangement can be made very cost-efficient and the X-ray detector of the imaging arrangement provides an excellent X-ray detector for cone beam CT scanning.

The present invention provides an imaging system with a detector that is almost blind to scattered X-rays without the need of a grid. By using line detectors the scattering problems as obtained in prior art systems are greatly reduced.

Further characteristics of the invention and advantages thereof will be evident from the detailed description of a preferred embodiment of the present invention given hereinafter and the accompanying drawings, which are only given by way of illustration, and thus are not limitative of the present invention.

BRIEF DESCRIPTION OF THE DRAWINGS

FIG. 5a is a top view of the X-ray detector of FIG. 3. FIG. 5b shows in a side view an elongated two-dimensional detector module as comprised in the X-ray detector of FIG. 5a, FIG. 5c shows the detector module in a top view; and FIG. 5d shows several detector modules placed short side to short side.

FIG. 6a is a top view of an X-ray detector of a computed tomography scanning system according to an alternative embodiment of the invention. FIG. 6b shows in a side view an elongated two-dimensional detector module as comprised in the X-ray detector of FIG. 6a, FIG. 6c shows the detector module in a top view; and FIG. 6d shows several detector modules placed long side to long side.

DETAILED DESCRIPTION OF EMBODIMENTS

In the following the present invention is described and exemplified by means of a particular medical application, namely mammography. The invention is however applicable in other medical areas as well as in other areas, such as baggage checking and material testing, with suitable modifications.

Mammography is an example of an important application of medical imaging. In a mammography procedure of today the breast of the patient is compressed between two compression plates and the X-ray source is activated and the X-ray detector captures a two-dimensional image of the breast. The compression of the breast is most uncomfortable to the patient. Further, it is important that the image quality is high, since breast cancer can, for example, be missed by being obscured by radiographically dense, fibrograndular breast tissue. There are thus a number of drawbacks related to the field of mammography. These drawbacks, among others, are overcome by means of the present invention.

Figure 1:
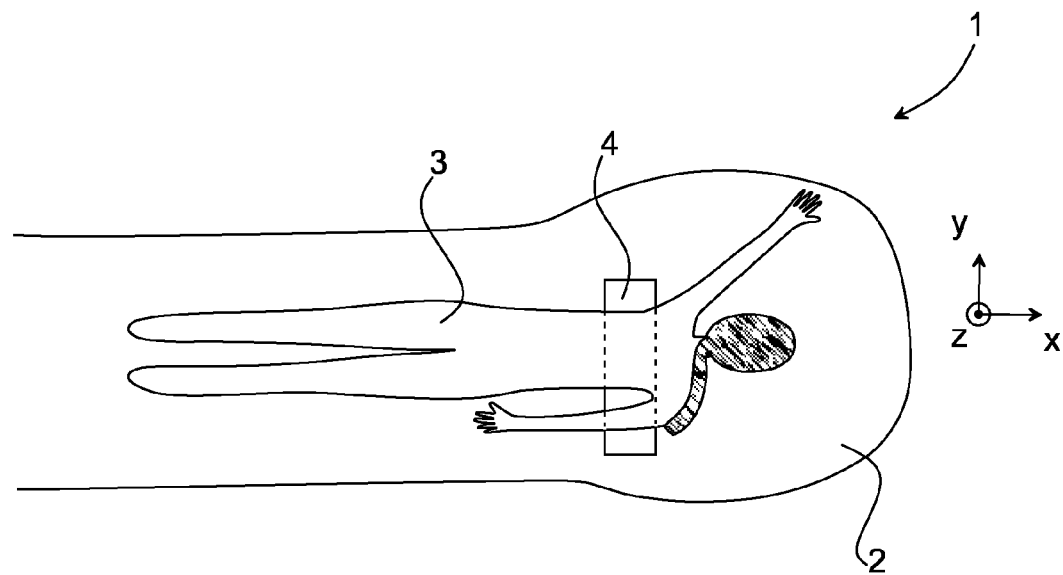
FIG. 1 is a top view of a patient positioning table as used in a computed tomography scanning system according to an embodiment of the invention.

FIG. 1 illustrates schematically the present invention in a mammography application. A computed tomography scanning system 1 for medical imaging comprises a horizontally arranged patient positioning table 2 on which the patient 3 rests face down. The patient thereby rests comfortably on a horizontal examination table during the whole examination. The patient positioning table 2 comprises a suitably located opening 4 in which the patient places her breasts.

Figure 2:
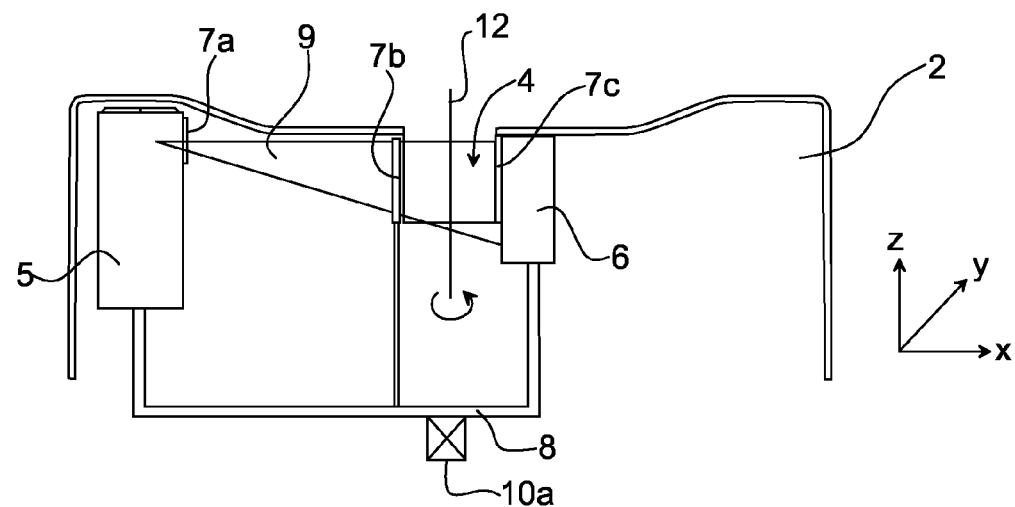
FIG. 2 is a side view of the computed tomography scanning system including the patient positioning table of FIG. 1.

FIG. 2 illustrates the system 1 of FIG. 1 in a side view. An imaging arrangement is provided underneath the patient positioning table 2. The imaging arrangement comprises an X-ray source 5, collimator 7a, multi slot collimators 7b-c, and an X-ray detector 6 attached to a support device 8, for example a common E-arm. The support device 8 is illustrated very schematically in the figure and it is realized that any suitable support structure may be utilized. The X-ray source 5 and the X-ray detector 6 are arranged on the support device 8 on opposite sides of the object to be imaged, the object being, in the illustrated example, the breast of a patient. The X-ray detector 6 is thereby able to measure the radiation emitted by the X-ray source 5 and transmitted through the breast of the patient 3.

The imaging arrangement, that is, the support device 8 comprising the X-ray source 5, the collimators 7a-c, and the X-ray detector 6 is rotated with respect to the object to be imaged by means of a rotating device 10a, e.g. a rotational motor device, while the X-ray detector 6 records images of the object repeatedly. The object, i.e. the breast, hangs down in a vertical direction while being imaged. There is no need to compress the breast but the breast should be held still during the procedure. The rotation axis of the imaging arrangement is vertical along the z axis through the breast and is indicated at 12.

Figure 3:
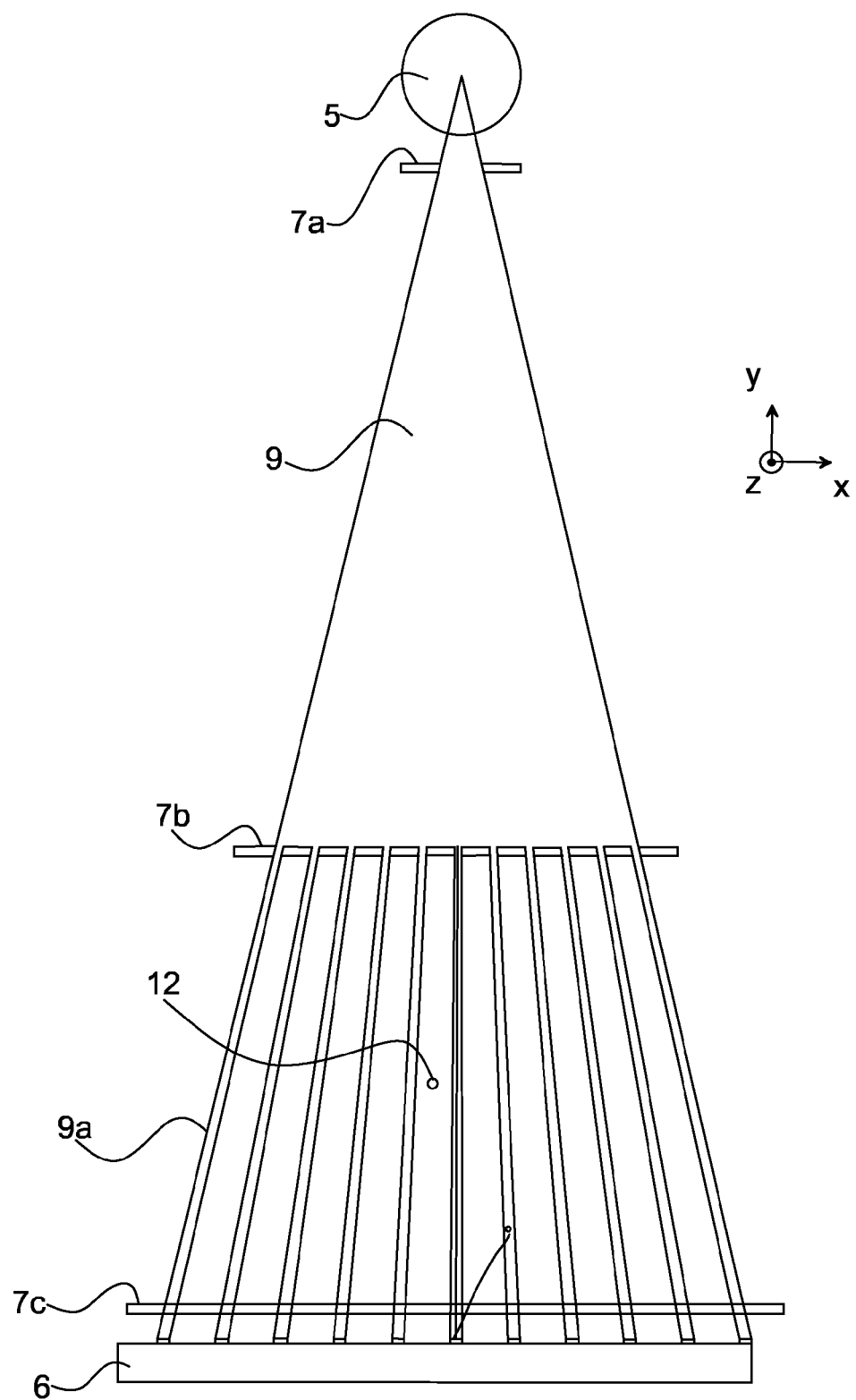
FIG. 3 is a top view of an X-ray source, collimators, and an X-ray detector as being comprised in the computed tomography scanning system of FIG. 2.

The X-ray source 5, the collimators 7a-c, and the X-ray detector 6 are illustrated more in detail in FIG. 3. The X-ray source 5 preferably comprises one or more X-ray tubes having a cathode, which emits electrons, and an anode, which emits X-rays in response to being struck by the electrons.

The collimators 7a-c may each be a thin foil of e.g. tungsten with suitable openings. The collimators 7a-b prevents radiation, which is not directed directly towards the X-ray detector 6, from impinging on the object, thereby reducing the radiation dose to the object. This is advantageous in particular in all applications where the object is a human or an animal, or parts thereof. Further, the downstream collimator 7c reduces scattered radiation from neighboring slots that otherwise would hit the X-ray detector 6.

The upstream collimator 7a operates as a screening device to limit the opening angle of the beam cone 9, whereas the other collimators 7b-c comprise slots to thereby create thin essentially planar sheets of radiation 9a. The size, design, and location of the slots are made such that the essentially planar sheets of radiation 9a impinge on individual detector modules of the X-ray detector 6.

Figure 4:
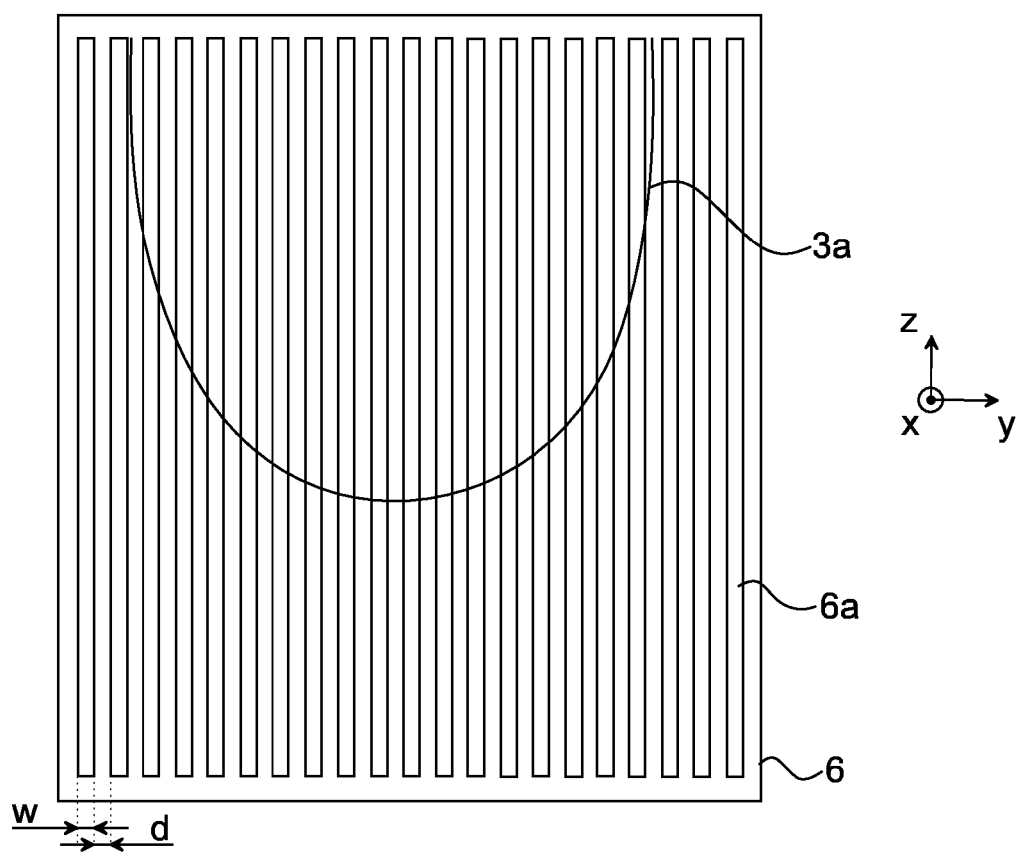
FIG. 4 is a side view of the X-ray detector of FIG. 3 wherein the contour of an object to be imaged is indicated.

The X-ray detector 6 is illustrated more in detail in FIG. 4 and comprises a stack of elongated detector array arrangements or line detectors 6a arranged in parallel and provided for detecting the essentially planar sheets of radiation 9a as transmitted through the object, thus recording images of the object. Each of the detector array arrangements 6a comprises preferably a plurality of elongated one- or two-dimensional detector modules arranged short side to short side. As such the X-ray detector 6 has a design with a stack of line detectors wherein each of the line detectors comprises several detector modules arranged up against each other in a row. Each line detector has a large number of pixels along its length and one or a modest number of pixels perpendicular thereto.

The distance d between each two adjacent ones of the elongated detector array arrangements 6a in a direction, i.e. y direction, essentially perpendicular to an optical axis, i.e. x direction, of the X-ray detector 6 is preferably less than or equal to the width w of the active detection areas of the elongated detector array arrangements.

FIG. 5a is a top view of the X-ray detector of FIG. 3. Preferably, detector array arrangements 6a are arranged on a support 6b or similar, which is moved by means of a moving device 10b, e.g. a linear motor device, during the rotation of the entire imaging arrangement to thereby cover the angles between adjacent ones of the detector array arrangements 6a. The detector array arrangements 6a are moved within the X-ray detector 6 linearly in a direction, i.e. the y direction, perpendicular both to the optical axis (the x direction) of the X-ray detector 6 and to the axis of rotation 12 (the z direction) during the rotation of the imaging arrangement. The movement may be performed continuously during the rotation or a stepwise linear movement is made after one revolution of rotation so that the "blind areas" between adjacent ones of the detector array arrangements 6a before the movement are covered by the detector array arrangements 6a after the movement. Thus, it is required here that the width w of the of the active detection areas of the detector array arrangements 6a is larger than the width d of the blind areas. Then, a further revolution of rotation may be performed. Hereby, sufficient computed tomography image data of the object can be obtained for generating a three-dimensional image of the object. Alternatively, if d is larger than w the rotation may be performed longer, i.e. if d=2*w three revolutions of rotation may be performed.

The computed tomography scanning system comprises preferably a computer or other device for calculating and generating such a three-dimensional image of the object from the computed tomography image data of the object. Preferably also, a display device is provided for displaying the generated image.

Alternatively, instead of moving the elongated detector array arrangements 6a within the X-ray detector 6 the axis of rotation 12 may be moved in a plane (the xy plane) which is essentially perpendicular to the axis of rotation 12 (the z direction) during the rotation of the imaging arrangement. Typically, the axis of rotation is moved in a circle so that images of the entire object are recorded at the different angles in order to thereby obtain sufficient computed tomography image data for generating a three-dimensional image of the object.

FIG. 5b shows in a side view an elongated two-dimensional detector module as comprised in each of the elongated detector array arrangements 6a of the X-ray detector 6, FIG. 5c shows the detector module in a top view; and FIG. 5d shows several detector modules placed short side to short side.

The detector module comprises preferably two printed circuit boards 51 arranged perpendicular to one another. An ASIC 52 is arranged on top of one of the printed circuit board 51, and a radiation sensitive detector array 53 is arranged on the ASIC 52. Appropriate electronic components 54 or circuitry may be arranged on the other printed circuit board. The radiation sensitive detector array 53 may be a Cd—Te or Cd—Zn—Te converter based detector array.

By way of example, the radiation sensitive detector array 53 of the detector module may be 6.4 mm wide and 25 mm long and comprise 64×250 pixels. Each elongated detector array arrangement or row 6a may consist of 12 detector modules arranged short side to short side to cover objects that is up to 300 mm in height. The X-ray detector may comprise 21 detector array arrangements or rows 6a with a distance of 6 mm between radiation sensitive detector arrays 53 of adjacent ones of the detector array arrangements or rows 6a.

A possible detector module is further disclosed in U.S. Pat. No. 5,379,336; U.S. Pat. No. 6,933,505; U.S. Pat. No. 7,170,062; U.S. Pat. No. 7,189,971; U.S. Pat. No. 7,361,881; US 2006/011853; US2006/071174; and US2008/019477, the contents of which being hereby incorporated by reference.

The detector module may alternatively be based on any other type of direction sensitive detector array based on for example PIN diodes, TFT, CCD or CMOS arrays.

Since the detector modules has circuitry, i.e. the ASIC 52, and the printed circuit board 51 protruding from the radiation sensitive detector array 53, some distance between radiation sensitive detector arrays 53 of adjacent ones of the detector array arrangements 6a is required, and therefore the movement of the detector array arrangements 6a or of the axis of rotation 12 is needed in addition to the rotation of the imaging arrangement in order to record images of the entire object at the different angles without obtaining any black spots or areas.

However, in a computed tomography scanning system according to an alternative embodiment of the invention as being illustrated in FIG. 6a the additional movement may be dispensed with.

Each of the elongated detector array arrangements 6a is radiation sensitive on an entire surface thereof except for a radiation blind stripe along one long side thereof. The elongated detector array arrangements 6a are arranged in different planes with an overlap between adjacent ones of the elongated detector array arrangements 6a such that the radiation blind stripes of all of the elongated detector array arrangements 6a but the two outermost ones are obscured by a radiation sensitive portion of an adjacent one of the elongated detector array arrangements 6a.

FIG. 6b shows in a side view an elongated two-dimensional detector module as comprised in the X-ray detector of FIG. 6a, FIG. 6c shows the detector module in a top view; and FIG. 6d shows several detector modules placed long side to long side.

The radiation blind stripes of the elongated detector array arrangements 6a comprise portions of a printed circuit board 61 and an ASIC 62 mounted on a first side of the printed circuit board 61. A radiation sensitive array 63 is mounted on the ASIC 62 and electronic components 64 or circuitries are mounted on a second side of the printed circuit board 61. Each elongated detector array arrangement 6a comprises here a number of detector modules arranged long side to long side. In FIG. 6d the radiation blind stripe of the elongated detector array arrangement 6a is shown to the right; exposed surfaces of the printed circuit boards 61 and the ASIC's 62.

In other respects the detector module may be similar to the one described with reference to FIGS. 5a-d.

In summary, by mean of the innovative imaging system new areas of application of CT-scanning are enabled. In particular, cone beam computed tomography is utilised in a mammography application. The present invention thus provides improvements of the examining of objects by means of cone beam computed tomography, wherein the time required for an examination is minimized. Further, the reliability of the results of an examination method is increased, while still minimizing the duration of the examination. In medical applications, the discomfort for a patient undergoing the examination is minimized, for example in that no compression of the breasts of a patient is needed.

The invention claimed is:

1. A computed tomography scanning system for recording computed tomography image data of an object in an object area, the system comprising:
   an X-ray source and an X-ray detector at either side of the object area, the X-ray source being configured for emitting X-rays and the X-ray detector comprising a stack of elongated detector array arrangements arranged in parallel separated from one another and being configured for detecting X-rays from the X-ray source transmitted through the object, thus recording images of the object;
   a device configured for rotating the X-ray source and the X-ray detector with respect to the object around an axis of rotation which is parallel with the elongated detector array arrangements arranged in parallel, while the elongated detector array arrangements are configured for imaging the object repeatedly;
   a multi slot collimator between the X-ray source and the object area to create thin essentially planar sheets of radiation, which impinge on the elongated detector array elements; and
   a device configured for moving the elongated detector array arrangements within the X-ray detector during the rotation of the X-ray source and the X-ray detector with respect to the object, thus allowing the elongated detector array arrangements to record the computed tomography image data of the object, wherein the device for moving the elongated detector array arrangements within the X-ray detector moves the elongated detector array arrangements linearly in a direction (y) perpendicular both to the optical axis (x) of the X-ray detector and to the axis of rotation (z) during the rotation of the X-ray source and the X-ray detector with respect to the object.

2. The system of claim 1 wherein the distance (d) between each of two adjacent ones of the elongated detector array arrangements in a direction essentially perpendicular to an optical axis of the X-ray detector is less than or equal to the width (w) of the active detection areas of the elongated detector array arrangements.

3. The system of claim 1 further comprising a multi slot collimator arranged between the X-ray source and the object area.

4. The system of claim 1 further comprising a multi slot collimator arranged between the object area and the X-ray detector.

5. The system of claim 1 wherein each of elongated detector array arrangements comprises a row of elongated detector arrays placed short side to short side.

6. The system of claim 1 wherein each of elongated detector array arrangements comprises a solid state detector array.

7. The system of claim 6 wherein the solid state detector array is a Cd—Te or Cd—Zn—Te based detector array.

8. The system of claim 1 further comprising a computer configured to generate a three-dimensional image of the object from the computed tomography image data of the object.

9. The system of claim 1 further comprising a patient positioning table.

10. The system of claim 9 wherein the object area is an opening in the patient positioning table, in which opening the object is positioned.

11. The system of claim 10 wherein the patient positioning table is horizontal and the X-ray source and the X-ray detector are arranged underneath the patient positioning table and arranged so as to record images of the object when placed in the opening.

12. The system of claim 1 wherein the system is configured for mammography.

13. A computed tomography scanning system for recording computed tomography image data of an object in an object area comprising:
   an X-ray source and an X-ray detector at either side of the object area, the X-ray source being configured for emitting X-rays and the X-ray detector comprising a stack of elongated detector array arrangements arranged in parallel separated from one another and being provided for detecting X-rays from the X-ray source transmitted through the object, thus recording images of the object;
   a device configured for rotating the X-ray source and the X-ray detector with respect to the object around an axis of rotation which is parallel with the elongated detector array arrangements arranged in parallel, while the elongated detector array arrangements are configured for imaging the object repeatedly;
   a multi slot collimator arranged between the X-ray source and the object area to create thin essentially planar sheets of radiation which impinge on the elongated detector array arrangements, the multi slot collimator, the X-ray source, and the X-ray detector being attached to an E-arm; and
   a device for moving the axis of rotation during the rotation of the X-ray source and the X-ray detector with respect to the object, thus allowing the elongated detector array arrangements to record the computed tomography image data of the object,
   wherein the device for moving the axis of rotation is configured for rotating axis of rotation in a plane (xy) essentially perpendicular to the axis of rotation during the rotation of the X-ray source and the X-ray detector with respect to the object.

14. A computed tomography scanning system for recording computed tomography image data of an object in an object area, the system comprising:
- an X-ray source and an X-ray detector at either side of the object area, the X-ray source being configured for emitting X-rays and the X-ray detector comprising a stack of elongated detector array arrangements arranged in parallel and being configured for detecting X-rays from the X-ray source transmitted through the object, thus recording images of the object; and
- a device configured for rotating the X-ray source and the X-ray detector with respect to the object around an axis of rotation which is parallel with the elongated detector array arrangements arranged in parallel, while the elongated detector array arrangements are configured for imaging the object repeatedly, wherein
- each of the elongated detector array arrangements is radiation sensitive on an entire surface thereof except for a radiation blind stripe along one long side thereof, and
- the elongated detector array arrangements are arranged in different planes with an overlap between adjacent ones of the elongated detector array arrangements such that the radiation blind stripes of all of the elongated detector array arrangements but the two outermost ones are obscured by a radiation sensitive portion of an adjacent one of the elongated detector array arrangements;
- wherein the elongated detector array arrangements are arranged such that the radiation blind stripes are arranged on an outer portion of the elongated detector array arrangements as seen from a central portion of the X-ray detector.

15. The system of claim 14 wherein each of elongated detector array arrangements comprises a solid state detector array.

16. The system of claim 15 wherein the solid state detector array is a Cd—Te or Cd—Zn—Te based detector array.

17. The system of claim 14 further comprising a patient positioning table.

18. The system of claim 17 wherein the object area is an opening in the patient positioning table, in which opening the object is positioned.

19. The system of claim 18 wherein patient positioning table is horizontal and the X-ray source and the X-ray detector are arranged underneath the patient positioning table and arranged so as to record images of the object when placed in the opening.

20. The system of claim 14 wherein the system is configured for mammography.

21. A computed tomography scanning system for recording computed tomography image data of an object in an object area, the system comprising:
- an X-ray source and an X-ray detector at either side of the object area, the X-ray source being configured for emitting X-rays and the X-ray detector comprising a stack of elongated detector array arrangements arranged in parallel and being configured for detecting X-rays from the X-ray source transmitted through said object, thus recording images of the object, and
- a device configured for rotating the X-ray source and the X-ray detector with respect to object around an axis of rotation which is parallel with the elongated detector array arrangements arranged in parallel, while the elongated detector array arrangements are configured for imaging the object repeatedly,
- wherein each of the elongated detector array arrangements is radiation sensitive on an entire surface thereof except for a radiation blind stripe along one long side thereof,
- the elongated detector array arrangements are arranged in different planes with an overlap between adjacent ones of the elongated detector array arrangements such that the radiation blind stripes of all of the elongated detector array arrangements but the two outermost ones are obscured by a radiation sensitive portion of an adjacent one of the elongated detector array arrangements, and
- the elongated detector array arrangements are tilted such that each elongated detector array arrangement has its radiation sensitive surface oriented perpendicular to the X-rays from the X-ray source transmitted through the object, which impinges on the radiation sensitive surface.

* * * * *